United States Patent [19]
Johnson

[11] Patent Number: 5,372,759
[45] Date of Patent: * Dec. 13, 1994

[54] METHOD OF HEAT TREATING GUTTA PERCHA BASED MATERIAL TO IMPROVE THE CHARACTERISTICS THEREOF FOR FILLING ENDODONTICALLY PREPARED ROOT CANALS

[76] Inventor: William B. Johnson, 5010 E. 68th St. Ste. 104, Tulsa, Okla. 74136

[*] Notice: The portion of the term of this patent subsequent to Feb. 15, 2011 has been disclaimed.

[21] Appl. No.: 140,782

[22] Filed: Oct. 21, 1993

Related U.S. Application Data

[62] Division of Ser. No. 889,828, May 29, 1992, Pat. No. 5,286,423.

[51] Int. Cl.$^5$ .................. A61C 13/00; B29C 71/02
[52] U.S. Cl. ...................... 264/16; 264/234; 264/345
[58] Field of Search .................. 264/16-20, 264/347, 345, 322, 40.1, 234; 433/81, 32, 224

[56] References Cited

U.S. PATENT DOCUMENTS

| | | |
|---|---|---|
| 2,899,402 | 8/1959 | Squire . |
| 3,863,345 | 2/1975 | Malmin . |
| 4,480,996 | 11/1984 | Crovatto . |
| 4,483,679 | 11/1984 | Fujisawa et al. . |
| 4,501,713 | 2/1985 | Wright . |
| 4,551,807 | 11/1985 | Hsich et al. . |
| 4,632,977 | 12/1986 | Riazi . |
| 4,758,156 | 7/1988 | Johnson . |
| 4,766,200 | 8/1988 | Riazi . |
| 4,894,011 | 1/1990 | Johnson . |
| 4,950,697 | 8/1990 | Chang et al. . |
| 4,966,952 | 10/1990 | Riaza . |
| 4,992,045 | 2/1991 | Beisel . |
| 5,061,411 | 10/1991 | Ubukata et al. . |
| 5,083,923 | 1/1992 | McSpadden . |
| 5,089,183 | 2/1992 | Johnson . |
| 5,098,298 | 3/1992 | Johnson . |

Primary Examiner—Karen Aftergut
Attorney, Agent, or Firm—Head & Johnson

[57] ABSTRACT

Material having improved characteristics for filling endodontically prepared root canals is obtained by heat treating gutta percha based material at a temperature in the range of 210° F. to 310° F. for a period of two to twenty-four hours, the time being decreased as the temperature is increased.

2 Claims, 1 Drawing Sheet

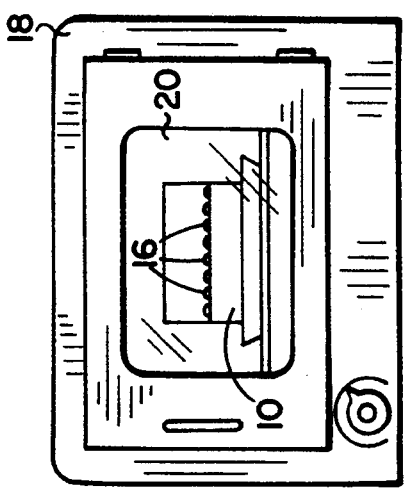

METHOD OF HEAT TREATING GUTTA PERCHA BASED MATERIAL TO IMPROVE THE CHARACTERISTICS THEREOF FOR FILLING ENDODONTICALLY PREPARED ROOT CANALS

This is a divisional application of copending application Ser. No. 07/889,828, filed May 29, 1992, now U.S. Pat. No. 5,286,423.

BACKGROUND OF THE INVENTION

This invention is related to a method of manufacturing appliances for use in filling endodontically prepared root canals as fully described in U.S. Pat. No. 5,089,183, issued Feb. 18, 1992. This patent, in turn, was related to a method of manufacturing appliances for filling endodontically prepared root canals of the type described in U.S. Pat. No. 4,758,156 entitled "Tool For Use In Applying Filler Material To An Endodontically Prepared Root Canal" issued Jul. 19, 1988 and U.S. Pat. No. 4,894,011 entitled "Appliance for Use In Applying Filler Material To An Endodontically Prepared Root Canal" issued Jan. 16, 1990. All of these previously issued patents are issued to Dr. William B, Johnson. Each of these three previously issued patents is incorporated herein by reference, This disclosure is specifically directed to improvements in the method described in U.S. Pat. No. 5,089,183 and is particularly concerned with heat treating of carrier material that contains gutta percha to provide a finished appliance for use in filling endodontically prepared root canals which is easier to use and more effective as an endodontic tool.

SUMMARY OF THE INVENTION

The essence of this disclosure is the provision of an improved method of manufacturing appliances for use in filling endodontically prepared root canals in which the finish product includes a filler material having enhanced properties that make it ideally suited for endodontic work. Most particularly, the completed product employing the method of this invention is a carrier having a shaft portion for insertion into an endodontically prepared root canal covered with a filler material formed thereon and in which the filler material, when heated such as in an oven or over an open bunsen burner, can be softened to a state for insertion into a tooth and in such softened state has increased flowability and adhesiveness so that it more effectively and permanently seals a root canal. The completed filler material has a lower melting point and lower molecular weight than the base material.

The method consists of eight basic steps. The first step is that of forming the filler material into a plurality of elongated slim points. These points are configured to that required for insertion into a root canal. Therefore the total volume of filler material in each point is at least equal to and preferably slightly greater than that which is required to fill the normal root canal. The filler material is of the type that includes gutta percha. Such material is frequently generically referred to as "gutta percha", but in actual practice the filler material most commonly favored today by endodontists is a formulated material having a gutta percha base with other constituents, such as zinc oxide, that make the material easier to use and more permanent when installed in a tooth.

Step 2 includes placing each of the formed points into an elongated cavity in a mold. The shape and dimension of the cavities is that which is required for the ultimate configuration of the appliance that is ready to be used by the endodontist. Typically, the cavities in the mold are slightly larger in their cross-sectional configurations than the preformed points so that the points will easily slip into the cavities. The typical mold includes a large number of cavities and the cavities need not necessarily all be the same size and length. A number of different sizes and lengths may be included in a single mold.

Step 3 is placing the mold having the points therein in an oven. The oven can be of any type that provides a controllable temperature with a fairly dependable degree of accuracy. The environment in the oven does not have to be specially treated, that is, it is not necessary that it be an inert environment.

Step 4 is subjecting the points while in the oven to a selected temperature for a selected time so that the filler material becomes plastic, that is, softens. As will be described in more detail subsequently, the essence of this invention is the discovery that the nature and quality of gutta percha based filler material can be substantially improved by subjecting the filler material to an elevated temperature for an extended length of time. When gutta percha based material is subjected to increased temperature over a fairly long duration a change in the characteristics of the material occurs. Others have recognized that gutta percha goes through a transition from one form or another. Reference may be had to U.S. Pat. No. 4,632,974 entitled "Method of Plasticizing Thermoplastic Polymers" issued Dec. 30, 1986. The essence of this patent is that the characteristics of certain polymers, including gutta percha, can be improved so that their thermal characteristics are changed. In this patent the treating process that results in the change of the thermal characteristics of the gutta percha based filler material is the step of very thoroughly masticating the material. While mastication is one means of changing and improving the characteristics of gutta percha based filler materials, the present invention is concerned with the fact that changes in the characteristics and quality of gutta percha materials can be obtained without such mastication. In step 4 the filler material is heated for a portion of the total time required to achieve the changes of characteristics that are required to improve the gutta percha based filler material. As will be pointed out subsequently, the time required to change the filler material characteristics is dependent upon the temperature to which it is subjected. It has been learned that in order to change the characteristics of the gutta percha material it must be heated to at least 210° F. for an extended length of time and should not be heated above 310° F. Thus, the material is heated within this range, that is, from 210° F. to 310° F. for a time duration varying between two hours and twenty-four hours—that length of time being inversely proportional to the temperature. As an example, if the material is subjected to a temperature of about 210° F. for about twenty to twenty-four hours the intended result is achieved. On the other hand, if the material is subjected to a high temperature such as that approaching 310° F. a time of only about two or three hours is required. In step 4 a fraction of this total length of time is employed and the other portion of the time is employed later in step number 7, which will be described subsequently.

After the gutta percha based filler material points are heated as described in step 4, step 5 requires the mold to be removed from the oven with the heated points in the mold cavities. The shaft portion of a filler carrier is then positioned in each cavity to partially displace the heated filler material therein. Each carrier has a handle portion that remains exterior of the mold.

Step 6 is that of placing the mold having filler material and the carriers back into the oven.

Step 7 continues the heat treatment process. The filler material and carriers in the mold are heated at the selected temperature mentioned in the description of step 4. The filler materials and carriers are heated for a length of time required to complete the total time desired depending upon the temperature selected. As an example, if the selected temperature of steps 4 and 7 is about 295° F. the total time required to achieve the desired change in the characteristic of the gutta percha material is about five to six hours. Two hours may be employed in step 4 and three or four hours in step 7. This is more or less arbitrary as this time ratio can be reversed. The only important thing is that step 4 should be carried out for a sufficient length of time that the filler material becomes sufficiently plastic to easily permit the shaft portion of each of the carriers to be inserted into the material within the cavities and for the material to expand to fill the cavities, with any overflow flowing out of the top of the cavities.

After the prescribed time has elapsed during which the filler material in the cavities is subjected to the desired temperature, the mold is removed from the oven as step No. 8. After the removal of the mold from the oven the mold is allowed to cool to or approach ambient temperature and the carriers having the filler material adhered thereto can be removed and are ready for use in filling an endodontically prepared canal.

Instead of treating the gutta percha based filler material in the form of points it may be treated in other shapes and subsequently used by a dentist or endodontist for direct placement in an endodontically prepared root canal without using a carrier. One way in which this can be accomplished is by placement of the treated filler material in a syringe from which it can be ejected onto a carrier or directly into a root canal.

DESCRIPTION OF THE DRAWINGS

FIG. 1 is an isometric view illustrating the mold which may be employed in practicing the method of this invention. The mold has a generally fiat upper surface having a plurality of spaced apart downwardly extending cavities therein. Each cavity is of a selected shape and length according to the ultimately desired appliance.

FIG. 2 shows the mold of FIG. 1 and the cavities therein, the mold being shown partially in cross-section, and showing the insertion of points of gutta percha based filler material being inserted into each of the cavities.

FIG. 3 is an elevational diagrammatic view of an oven having the mold of FIGS. 1 and 2 therein with gutta percha points positioned in each of the cavities in the mold.

FIG. 4 is an enlarged cross-sectional elevational view of a portion of the mold of FIGS. 1 and 2 showing the shape of one of the cavities and showing the cavity filled with gutta percha based filler material in the configuration after the mold has been heated to change the filler material to a plastic state.

FIG. 5 shows the mold in cross-section as in FIG. 4 having been removed from the oven and the shaft portion of a carrier element inserted into the mold cavity. The shaft partially displaces the heated, plastic state, filler material.

FIG. 6 shows the mold placed back into the oven, the mold cavities being filled with gutta percha based filler material and with the shaft portion of the carriers positioned in the mold for continued heating of the filler material.

FIG. 7 shows the completed appliance ready for use in filling an endodontically prepared root canal after it has been manufactured following the method of this invention.

DESCRIPTION OF THE PREFERRED EMBODIMENT

Referring to the drawing the items necessary for practicing this invention are illustrated more or less diagrammatically but in sufficient detail to enable one skilled in the art to practice the invention. FIG. 1 shows a mold 10 having an upper surface 12 and a plurality of elongated cavities 14 communicating with the upper surface. The cavities are tapered, however, this is by way of example only as the cavities can be cylindrical. While tapered cavities are preferred, the invention is not limited to this arrangement. FIG. 2 shows mold 10 in an elevational, partially cross-section view revealing the general shape of cavities 14. FIG. 2 also shows points of filler material 16. The points of filler material are configured to fit into cavities 14. When the cavities are tapered, as illustrated, points 16 are likewise tapered. If the cavities are cylindrical, the points should then also be cylindrical. Points 16 are formed of filler material that is customarily utilized for filling an endodontically prepared root canal. The most common type of materials utilized for this purpose are based upon gutta percha. Usually the filler material is gutta percha combined with other ingredients, such as zinc oxide and other additives, to form a filler material that is easier to use and longer lasting than the pure gutta percha as derived as an organic substance. Points 16 as formulated of gutta percha based filler material are commercially available from a number of suppliers that process gutta percha. Gutta percha based filler material in points as illustrated, or in other bulk forms, is supplied directly to endodontists for use in filling root canals or is supplied to manufacturers of appliances for use in filling root canals. The exact formulation of the gutta percha based filler material points 16 varies from manufacturer to manufacturer and is usually maintained as trade secrets. The method of this invention is intended to provide a method of making an improved appliance for use in filling endodontically prepared root canals and particularly wherein the filler material has improved characteristics to ensure that a root canal filled with the appliance is less likely to fail.

As shown in the left-hand portion of FIG. 2, gutta percha based filler material tips 16 are positioned in each of the cavities 14. After the cavities in mold 10 have been filled with the gutta percha based filler material points, the mold is positioned in an oven as illustrated in FIG. 3, the oven being indicated by the numeral 18. The oven has a window 20 so that mold 10 having the gutta percha(based) filler material points 16 therein can be seen through the window.

The essence of this invention is the discovery that the quality and characteristics of gutta percha based filler material can be substantially enhanced by heat treating the filler material at an elevated temperature and for an extended length of time. Others have known that the quality and characteristics of gutta percha based filler material can be changed by treatment, and reference has previously been made to U.S. Pat. No. 4,632,977 wherein the gutta percha based filler material is altered by thoroughly masticating the material. The altered characteristics of the material are emphasized by the dramatic change in the melt point index of the material after it has been masticated for a selected length of time. This disclosure is based on the discovery that essentially the same results are obtained, not by mastication, but instead, by simply heating the gutta percha based material at an elevated temperature for an extended length of time.

In the method of the invention herein the gutta percha based material is heated at a temperature of at least 210° F. and not more than 310° F. for an extended length of time. The time required to effect the quality and characteristic change desired of the gutta percha based filler material varies from about two hours to about twenty-four hours; the higher the temperature the shorter the duration of treatment.

FIG. 4 is an enlarged fragmentary view of mold 10 showing a tapered point 16 positioned within a cavity 14. After the mold having the taper points of gutta percha based material therein has been in the oven for a length of time sufficient to raise the temperature of the gutta percha based material to the point where it becomes plastic, that is, pliable, the mold is removed from the oven and the shaft portion of a dental appliance is inserted into each of the mold cavities.

FIG. 5 shows a dental appliance 22 with the shaft portion 24 inserted into cavity 14 in mold 10 partially displacing some of the filler material 16. The carrier 22 has a handle 26 that remains external of the mold.

After the shaft portion of the carriers are inserted into each of the mold cavities, the mold is placed back in the oven as shown in FIG. 6. Through window 20 mold 10 is seen with handle portions 26 of the carriers extending upwardly above the top surface of the mold. The mold is kept in the oven so that the total heat treating time is that which is required to achieve the desired end result, that is, the heat treat time is divided into two portions, the first portion taking place when the mold is in the oven as in FIG. 3 and the second portion when the mold is in the oven as in FIG. 6. The time duration of these two portions can be divided in nearly anyway desired as long as the mold is left in the oven as in FIG. 3 for a sufficient time that the gutta percha based material becomes heated to increase the plasticity to allow for easy insertion of the carrier shaft portions.

The total treatment time in the oven depends, as previously indicated, upon the temperature at which the material is treated. If the temperature is about 210° F. the total treatment time must total about 24 hours. On the other hand, if the temperature of treatment is about 310° F. the total treatment time need only be about two hours. A preferred arrangement is that in which the treatment temperature is set at about 295° F. and the total treatment time of the two steps is about five hours. When the total time in the oven is about five hours it can be divided into a first period of two hours in which only the points are heated, followed by a second period of three hours after the carriers are inserted.

After the total heat treatment time has been concluded, the mold is removed from the oven and permitted to return to ambient temperature. After it has returned to ambient temperature the carriers having the gutta percha based filler material 16A adhered thereto are removed from the mold to provide a finished appliance, indicated by the numeral 28 in FIG. 7.

The appliance 28 of FIG. 7 is ready to be used by an endodontist for filling a root canal. The appliance is used by warming the gutta percha based filler material 16A, such as over a bunsen burner or in an oven, to raise the temperature thereof so that it attains a plastic state. The shaft portion having the heated filler material thereon is inserted into the root canal and the shaft portion severed and left in the root canal along with the filler material. The filler material having been heat treated according to the process described herein has highly improved characteristics compared to that of the gutta percha based points obtained directly from a supplier. The heat treated filler material has improved flow properties when heated over a bunsen burner or in an oven prior to insertion into a root canal and, in addition, has much better adhesiveness. The improved flow properties ensure that the root canal, including ancillary passageways, are more effectively filled by the filler material. The improved adhesiveness ensures that the filler material remains securely in place within the prepared root canal and in firm engagement with the carriers shaft portion 24 that also remains in the root canal.

The method of this invention may be used to provide improved filler material that is not formed onto a carrier, in which case the gutta percha based filler material does not start in the form of points, as has been described, but instead may be in bulk form without any particular shape. The bulk gutta percha based filler material is heated in oven 18 at temperatures and times above described to cause the material's characteristics to change in the same way as has been described with reference to points 16. In treating bulk gutta percha based filler material wherein a carrier is not involved, the heat treating step does not have to be broken into two portions as has been previously described.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A method of treating gutta percha based filler material to improve characteristics thereof for use in filling endodontically prepared root canals, without masticating the filler material, the method comprising the steps of:
    (a) placing the gutta percha based filler material into an oven;
    (b) heating the oven to a temperature of at least 210° F. and not more than 310° F. for a length of time of between about 2 hours and 24 hours to thereby heat the filler material to substantially the same temperature and for the same length of time without mastication to improve the characteristics of the filler material, the length of time being decreased as the temperature is increased; and (c) removing the heated filler material having the improved characteristics from the oven, the filler material being ready for use to fill endodontically prepared root canals.

2. A method of heat treating gutta percha based filler material according to claim 1 wherein in step (b) the temperature is about 295° F. and wherein the length of time is about 5 hours.

* * * * *